United States Patent
Craig et al.

(10) Patent No.: US 8,071,662 B2
(45) Date of Patent: Dec. 6, 2011

(54) DENTAL COMPOSITIONS WITH SURFACE-TREATED FILLER FOR SHELF STABILITY

(75) Inventors: Bradley D. Craig, Cottage Grove, MN (US); Brian A. Shukla, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 12/159,237

(22) PCT Filed: Dec. 28, 2006

(86) PCT No.: PCT/US2006/049463
§ 371 (c)(1),
(2), (4) Date: Jun. 26, 2008

(87) PCT Pub. No.: WO2007/079166
PCT Pub. Date: Jul. 12, 2007

(65) Prior Publication Data
US 2008/0293846 A1 Nov. 27, 2008

Related U.S. Application Data

(60) Provisional application No. 60/754,985, filed on Dec. 29, 2005.

(51) Int. Cl.
*A61K 6/08* (2006.01)
(52) U.S. Cl. ...................................... 523/116
(58) Field of Classification Search .............. 523/109, 523/113, 114, 115, 116, 118, 117, 120
See application file for complete search history.

(56) References Cited

U.S. PATENT DOCUMENTS

| | | | |
|---|---|---|---|
| 4,259,075 A | 3/1981 | Yamauchi et al. | |
| 4,298,738 A | 11/1981 | Lechtken et al. | |
| 4,324,744 A | 4/1982 | Lechtken et al. | |
| 4,356,296 A | 10/1982 | Griffith et al. | |
| 4,385,109 A | 5/1983 | Lechtken et al. | |
| 4,499,251 A | 2/1985 | Omura et al. | |
| 4,503,169 A | 3/1985 | Randklev | |
| 4,514,342 A | 4/1985 | Billington et al. | |
| 4,537,940 A | 8/1985 | Omura et al. | |
| 4,539,382 A | 9/1985 | Omura et al. | |
| 4,588,756 A | 5/1986 | Bowen et al. | |
| 4,629,746 A | 12/1986 | Schaan et al. | |
| 4,642,126 A | 2/1987 | Zador et al. | |
| 4,648,843 A | 3/1987 | Mitra | |
| 4,652,274 A | 3/1987 | Boettcher et al. | |
| 4,665,217 A | 5/1987 | Reiners et al. | |
| 4,695,251 A | 9/1987 | Randklev | |
| 4,710,523 A | 12/1987 | Lechtken et al. | |
| 4,737,593 A | 4/1988 | Ellrich et al. | |
| 4,752,338 A | 6/1988 | Reiners et al. | |
| 4,767,798 A | 8/1988 | Gasser et al. | |
| 4,872,936 A | 10/1989 | Engelbrecht | |
| 5,026,902 A | 6/1991 | Fock et al. | |
| 5,076,844 A | 12/1991 | Fock et al. | |
| 5,130,347 A | 7/1992 | Mitra | |
| 5,154,762 A | 10/1992 | Mitra et al. | |
| 5,501,727 A | 3/1996 | Wang et al. | |
| 5,530,038 A | 6/1996 | Yamamoto et al. | |
| 5,545,676 A | 8/1996 | Palazzotto et al. | |
| 5,684,060 A | 11/1997 | Konings et al. | |
| 6,030,606 A | 2/2000 | Holmes | |
| 6,187,833 B1 | 2/2001 | Oxman et al. | |
| 6,251,963 B1 | 6/2001 | Kohler et al. | |
| 6,306,926 B1 | 10/2001 | Bretscher | |
| 6,386,203 B1 | 5/2002 | Hammerslag | |
| 6,387,981 B1 * | 5/2002 | Zhang et al. | 523/117 |
| 6,458,868 B1 | 10/2002 | Okada et al. | |
| 6,572,693 B1 | 6/2003 | Wu et al. | |
| 6,703,518 B1 * | 3/2004 | Xu et al. | 556/56 |
| 6,730,156 B1 | 5/2004 | Windisch | |
| 6,747,071 B1 | 6/2004 | Frances | |
| 6,790,877 B2 * | 9/2004 | Nakatsuka et al. | 523/118 |
| 6,899,948 B2 | 5/2005 | Zhang | |
| 6,984,673 B2 * | 1/2006 | Kawashima et al. | 523/116 |
| 7,026,367 B2 * | 4/2006 | Kalgutkar | 522/31 |
| 7,037,583 B2 * | 5/2006 | Furman et al. | 428/403 |
| 7,226,960 B2 * | 6/2007 | Jia | 523/115 |
| 7,449,499 B2 | 11/2008 | Craig et al. | |
| 7,452,924 B2 | 11/2008 | Aasen et al. | |
| 2002/0156152 A1 | 10/2002 | Zhang | |
| 2003/0018098 A1 * | 1/2003 | Falsafi et al. | 523/116 |
| 2003/0055123 A1 * | 3/2003 | Kawashima et al. | 523/116 |
| 2003/0166737 A1 | 9/2003 | Dede et al. | |
| 2003/0166740 A1 | 9/2003 | Mitra et al. | |
| 2003/0171505 A1 | 9/2003 | Bublewitz et al. | |
| 2003/0195273 A1 | 10/2003 | Mitra et al. | |

(Continued)

FOREIGN PATENT DOCUMENTS

EP 0 173 567 3/1986

(Continued)

OTHER PUBLICATIONS

Moszner et al., "Chemical aspects of self-etching enamel-dentin adhesives: A systematic review," *Dental Materials*, 2005; 21:895-910.
Salz et al., "Adhesion Performance of New Hydrolytically Stable One-component Self-etching Enamel/Dentin Adhesives," *The Journal of Adhesive Dentistry*, 2010;12(1):7-11.
Weinburg, Ed., Technique of Electroorganic Synthesis Part II Techniques of Chemistry, vol. V (1975).
Mann et al., Electrochemical Reactions in Nonaqueous Systems, 1970.
Merck (2-hydroxypropyl methacrylate data sheet); p. 1-3. www://merck-chemicals.com/hydroxypropyl-methacrylate/MDA_CHEM-800610/p..., retrieved Jul. 14, 2010.
International Preliminary Report on Patentability (including the Written Opinion for International application No. PCT/US2006/049249, 5 pages,(May 31, 2007).
Written Opinion of the International Searching Authority for International Application No. US2006/049427, 4 pages, (Jun. 5, 2007).
Written Opinion of the International Searching Authority for International Application No. US2006/049463, 4 pages, (May 31, 2007).

*Primary Examiner* — Mark Eashoo
*Assistant Examiner* — David Karst

(57) ABSTRACT

The invention features dental compositions containing a basic filler that has been surface-treated with a strong acid to increase the shelf life of the composition.

9 Claims, No Drawings

U.S. PATENT DOCUMENTS

| | | |
|---|---|---|
| 2004/0014009 A1* | 1/2004 | Jia et al. .................. 433/215 |
| 2004/0110864 A1 | 6/2004 | Hecht |
| 2004/0235981 A1* | 11/2004 | Qian ....................... 523/115 |
| 2005/0070627 A1 | 3/2005 | Falsafi et al. |
| 2005/0175965 A1* | 8/2005 | Craig et al. ............... 433/215 |
| 2005/0175966 A1 | 8/2005 | Falsafi et al. |
| 2005/0176844 A1* | 8/2005 | Aasen et al. ............... 523/118 |
| 2005/0252413 A1 | 11/2005 | Kangas et al. |
| 2005/0252414 A1 | 11/2005 | Craig et al. |
| 2005/0252415 A1* | 11/2005 | Budd et al. ................ 106/35 |
| 2005/0256223 A1 | 11/2005 | Kolb et al. |
| 2006/0084717 A1* | 4/2006 | Cohen et al. ............... 523/116 |
| 2006/0144726 A1 | 7/2006 | Foust et al. |
| 2006/0144733 A1 | 7/2006 | Wu et al. |
| 2007/0243145 A1* | 10/2007 | Andre et al. ............... 424/59 |
| 2007/0248927 A1 | 10/2007 | Luchterhandt et al. |
| 2008/0193759 A1* | 8/2008 | Rieger et al. .............. 428/402 |
| 2008/0293846 A1 | 11/2008 | Craig |
| 2008/0306168 A1 | 12/2008 | Craig et al. |
| 2009/0005469 A1 | 1/2009 | Craig et al. |
| 2009/0047486 A1 | 2/2009 | Jones et al. |
| 2009/0075239 A1 | 3/2009 | Abuelyaman |

FOREIGN PATENT DOCUMENTS

| | | |
|---|---|---|
| EP | 189540 | 8/1986 |
| EP | 0 201 031 | 11/1986 |
| EP | 0 201 778 | 11/1986 |
| EP | 0 373 384 | 6/1990 |
| EP | 712622 | 5/1996 |
| EP | 1 051 961 | 11/2000 |
| EP | 1586294 | 10/2005 |
| EP | 238025 | 9/2007 |
| WO | WO 00/38619 | 7/2000 |
| WO | WO 00/42092 | 7/2000 |
| WO | WO 01/07444 | 2/2001 |
| WO | WO 01/30305 | 5/2001 |
| WO | WO 01/92271 | 12/2001 |
| WO | WO 03/063804 | 8/2003 |
| WO | WO 2007/079070 | 7/2007 |
| WO | WO 2007/079144 | 7/2007 |
| WO | WO 2007/079166 | 7/2007 |
| WO | WO 2009/152211 | 12/2009 |

* cited by examiner

DENTAL COMPOSITIONS WITH SURFACE-TREATED FILLER FOR SHELF STABILITY

CROSS REFERENCE TO RELATED APPLICATIONS

This application is a national stage filing under 35 U.S.C. 371 of PCT/US2006/049463, filed Dec. 28, 2006, which claims benefit to U.S. Provisional Application No. 60/754,985, filed Dec. 29, 2005, the disclosure of which is incorporated by reference in its entirety herein.

FIELD OF THE INVENTION

The present invention relates to dental compositions, including polymerizable dental compositions, that contain a surface-treated filler.

BACKGROUND

The restoration of dental structures, including caries, decayed dentin, or decayed enamel, is often accomplished by the sequential application of a dental adhesive followed by a dental material (e.g., a restorative material) to the relevant dental structures. Similarly, adhesives are also used in the bonding of dental materials (e.g., orthodontic appliances, generally utilizing an orthodontic adhesive) to a dental structure. Often various pretreatment processes are used to promote the bonding of dental adhesives to dentin or enamel. Typically, such pretreatment steps include etching using, for example, inorganic or organic acids, followed by priming to improve the bonding between the tooth structure and the overlying adhesive.

Whether for application of dental restoratives (e.g., cured or uncured composites such as glass ionomer cements, modified glass ionomer cements, etc.; fillings; sealants; inlays; onlays; crowns; bridges; etc.) or orthodontic appliances to a dental structure surface, the etchants, primers, and adhesives are typically applied in a step-wise fashion. Often between such steps, one or more rinsing and drying steps are used. As a result, dental restoration and the application of orthodontic appliances typically involve multi-step procedures.

In order to reduce the complexity, difficulty, and time required to perform such procedures, recent efforts have been made to combine two or more of these steps together in a single step by providing compositions that perform multiple functions. For example, efforts have been made to develop self-etching adhesives, i.e., adhesive compositions in which a single composition is able to perform the etching, priming, and adhesive functions in a single step. One of the problems associated with the development of suitable self-etching adhesive formulations is that the combinations of components typically used in such compositions are not always stable, which can lead to reduced shelf life of the composition. Consequently, there is a need for a means to provide self-etching adhesive compositions that have sufficient stability and shelf life to be useful in the typical dental and/or orthodontic practice.

SUMMARY OF THE INVENTION

The present invention features hardenable dental compositions that contain a polymerizable component, and a basic filler that has been surface-treated with an acidic component, i.e. an acidic component is attached to the surface of the filler. Typically, the acidic component comprises a strong acid, such as a carboxylic acid or sulfonic acid, including a sulfonic acid methacrylate derivate, such as sulfoalkyl methacrylate, e.g. sulfopropyl methacrylate or the like.

The polymerizable component typically comprises an ethylenically unsaturated component, preferably a phosphorylated monomer, such as a phosphorylated methacrylate. The basic filler typically comprises at least one metal oxide particle, such as zirconia, alumina, ytterbia, zinc, etc. or combinations thereof. Preferably, the particles comprise nano-sized particles.

The surface-treated filler used in the compositions of the invention may be prepared by a method comprising the steps of: (a) providing a metal oxide particle having a surface, (b) admixing the metal oxide particle with a salt that comprises an acidic component, thereby forming a mixture, and (c) contacting the mixture with an ion-exchange resin to attach the acidic component to the surface of the metal oxide particle. This method provides a relatively simple and convenient way of applying, for example, a strong acid (meth)acrylate onto the surface of, for example, nanozironia through an ion exchange of a salt.

In some implementations, the composition of the present invention is a non-aqueous, self-etching adhesive that can be used for bonding a dental material to a dental structure. Surfaces (e.g., cut or uncut) of such dental structures include, for example, enamel, dentin, and cementum. Exemplary dental materials include, for example, dental restoratives, orthodontic adhesives, and orthodontic appliances (e.g., including orthodontic appliances precoated with a cured or uncured orthodontic adhesive). Optionally, the adhesive composition is substantially free of organic solvents. Typically, the non-aqueous dental adhesive includes an ethylenically unsaturated compound with acid functionality, an ethylenically unsaturated compound without acid functionality, and an initiator system.

When such compositions are loaded with the surface-treated filler (e.g. nanozirconia with a strong acid (meth)acrylate attached to its surface) the composition typically exhibits an increase in adhesion performance on a dentin substrate. The filler also allows for rheology modification and/or potential radiopacity of the composition when used at sufficiently high quantities (e.g. generally equal to or greater than about 20 wt-% surface-treated filler).

In addition, the dental compositions of the invention typically exhibit a longer effective shelf life (i.e., the adhesive remains effective longer) than they would without the use of a surface-treated filler as a stabilizing agent. Typically, the compositions of the present invention have a shelf life of at least 12 weeks at 45° C., more typically at least 16 weeks at 45° C., and most typically at least 20 weeks at 45° C. For example, this allows a dentist or orthodontist to store the product for longer periods of time before using or reducing the likelihood that the practitioner will need to replace the product before it has been used up.

The above summary is not intended to describe each embodiment or every implementation of the invention. Other embodiments, features, and advantages of the present invention will be apparent from the following detailed description thereof, and from the claims.

DEFINITIONS

As used herein, "adhesive" or "dental adhesive" refers to a composition used on a dental structure (e.g., a tooth) to adhere a "dental material" (e.g., "restorative," an orthodontic appliance (e.g., bracket), or an "orthodontic adhesive") to the dental structure. An "orthodontic adhesive" refers to a highly (generally greater than 40% by weight) filled composition (more analogous to a "restorative material" than to a "dental adhesive") used to adhere an orthodontic appliance to a dental structure (e.g., tooth) surface. Generally, the dental structure surface is pre-treated, e.g., by etching, priming, and/or applying an adhesive to enhance the adhesion of the dental or orthodontic adhesive to the dental structure surface.

As used herein, a "non-aqueous" composition (e.g., an adhesive) refers to a composition in which water has not been added as a component. However, there may be adventitious water in other components of the composition, but the total amount of water typically does not exceed about 1.5%. Non-aqueous compositions preferably include less than 1% by weight, more preferably less than 0.5% by weight, and most preferably less than 0.1% by weight water, based on the total weight of the non-aqueous composition.

As used herein, a "self-etching" composition refers to a composition that bonds to a dental structure surface without pretreating the dental structure surface with an etchant. In some embodiments, a self-etching composition can also function as a self-primer wherein no separate etchant or primer are used.

As used herein, a "self-adhesive" composition refers to a composition that is capable of bonding to a dental structure surface without pretreating the dental structure surface with a primer or bonding agent. In some embodiments, a self-adhesive composition is also a self-etching composition wherein no separate etchant is used.

As used herein, "hardening" or "curing" a composition are used interchangeably and refer to polymerization and/or crosslinking reactions including, for example, photopolymerization reactions and chemical polymerization techniques (e.g., ionic reactions or chemical reactions forming radicals effective to polymerize ethylenically unsaturated compounds) involving one or more materials included in the composition.

As used herein, a "dental structure surface" refers to tooth structures (e.g., enamel, dentin, and cementum) and bone.

As used herein, "dental material" refers to a material that may be bonded to a dental structure surface and includes, for example, dental restoratives, orthodontic appliances, and/or orthodontic adhesives.

By "basic filler" is meant a particulate dental filler material (e.g., metal oxides such as zirconia) suitable for use in the oral environment wherein the surface of the material is basic in character due to the presence of atoms having an unshared pair of electrons.

By "acidic component" is meant a compound or material comprising atoms capable of accepting an unshared pair of electrons, e.g. a compound having a proton, such as a carboxylic or sulfonic acid.

By "strong acid" is meant that the acidic component is preferably stronger than mono-2-(methacyloyloxy)ethyl succinate, or typically has a pKa lower than about 5. In some embodiments, the strong acid has a pKa lower than about 4.

By "sulfonic acid methacryoyl derivative" is meant a compound having a structure that includes both a sulfonic acid group and a (meth)acryloyl group (e.g., a (meth)acrylate group, a (meth)acrylamide group, and the like).

By "filler" is meant a particulate dental material suitable for use in the oral environment. Dental fillers generally have an average particle size of at most 100 micrometers.

By "nanofiller" is meant a filler having an average primary particle size of at most 200 nanometers. The nanofiller component may be a single nanofiller or a combination of nanofillers. Typically the nanofiller comprises non-pyrogenic nanoparticles or nanoclusters.

As used herein "nanoparticles" is used synonymously with "nanosized particles," and refers to particles having an average size of at most 200 nanometers. As used herein for a spherical particle, "size" refers to the diameter of the particle. As used herein for a non-spherical particle, "size" refers to the longest dimension of the particle.

As used herein "ethylenically unsaturated component" refers to a monomer, oligomer, and polymer having at least one ethylenic unsaturation. The ethylenically unsaturated component may be a single ethylenically unsaturated compound or a mixture of one or more ethylenically unsaturated compounds.

As used herein, "phosphorylated monomer" refers to a monomer (e.g. a (meth)acrylate) that comprises at least one phosphate or phosphonate group.

As used herein, "(meth)acryl" is a shorthand term referring to "acryl" and/or "methacryl." For example, a "(meth)acryloyloxy" group is a shorthand term referring to either an acryloyloxy group (i.e., $CH_2=CHC(O)O-$) and/or a methacryloyloxy group (i.e., $CH_2=C(CH_3)C(O)O-$); and a "(meth)acryloyl" group is a shorthand term referring to either an acryloyl group (i.e., $CH_2=CHC(O)-$) and/or a methacryloyl group (i.e., $CH_2=C(CH_3)C(O)-$).

The term "dental composition" as used herein also includes orthodontic compositions.

The recitation of numerical ranges by endpoints includes all numbers subsumed within that range (e.g. 1 to 5 includes 1, 1.5, 2, 2.75, 3, 3.80, 4, and 5).

As used herein, "a" or "an" means "at least one" or "one or more" unless otherwise indicated. In addition, the singular forms "a", "an", and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

Unless otherwise indicated, all numbers expressing quantities of ingredients, measurement of properties such as contrast ratio and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

DETAILED DESCRIPTION

The present invention features polymerizable dental compositions that contain a basic filler (e.g. nanozirconia) that has been surfaced treated with an acidic component (e.g. a strong acid (meth)acrylate or strong carboxylic acid). The addition of the surface-treated filler to a polymerizable dental composition, particularly to non-aqueous dental and/or orthodontic adhesives that contain a phosphorylated monomer, can increase the stability and shelf life of the composition. It is particularly advantageous to incorporate a water scavenger into a self-etching and/or self-adhesive composition, such as those described in, for example, U.S. Pat. Publication Nos. 2005/0175965 (Craig et al.), 2005/0175966 (Falsafi et al.), and 2005/0176844 (Aasen et al.) Such self-etching primer and self-etching adhesive compositions are typically prepared by combining polymerizable components (e.g., ethylenically unsaturated compounds with acid functionality and ethylenically unsaturated compounds without acid functionality) and an initiator system. Typically, the selection of polymerizable components is made to impart the desired etching, priming, adhesive, and/or restorative properties to the compositions. Generally, techniques for selecting polymerizable components and other optional components to impart etching, priming, adhesive, and/or restorative properties to hard-surface treatment compositions are well known to those skilled in formulation of dental materials. Suitable polymerizable components for use in such compositions, dental adhesives, and dental restoratives are discussed in more detail below.

In some embodiments, the compositions are hardened (e.g., polymerized by conventional photopolymerization and/or chemical polymerization techniques) prior to applying the dental material. In other embodiments, the compositions are hardened after applying the dental material. For embodiments in which the composition is an adhesive, it is advantageous if it is formulated to promote adhesion to both enamel and dentin. It is particularly advantageous if the composition is formulated to function as the etchant, primer, and adhesive to both enamel and dentin. It is also desirable to provide compositions that can function as the etchant, primer, adhesive, and restorative material (or orthodontic adhesive) for both enamel and dentin.

Compositions of the present invention can optionally include fillers, surfactants, solvents, and other additives. Various combinations of the components described herein can be used in the compositions of the present invention.

Certain non-aqueous compositions (typically include less than 1% by weight water in the composition) of the present invention have enhanced chemical stability. That is, they have, for example, a room-temperature shelf-life stability of at least 1 year, and preferably at least 2 years.

Polymerizable Component

Suitable polymerizable components that can be used in dental materials and dental adhesive compositions in the methods of the present invention include epoxy resins (which contain cationically active epoxy groups), vinyl ether resins (which contain cationically active vinyl ether groups), ethylenically unsaturated compounds (which contain free radically active unsaturated groups, e.g., acrylates and methacrylates), and combinations thereof. Also suitable are polymerizable materials that contain both a cationically active functional group and a free radically active functional group in a single compound. Examples include epoxy-functional (meth)acrylates.

In a one embodiment, the polymerizable component comprises a phosphorylated monomer. Preferably, the polymerizable component comprises one or more ethylenically unsaturated compounds, with or without acid functionality, that is phosphorylated, such as a phosphorylated methacrylate.

Ethylenically Unsaturated Compounds With Acid Functionality

As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates.

Ethylenically unsaturated compounds with acid functionality include, for example, α,β-unsaturated acidic compounds such as glycerol phosphate mono(meth)acrylates, glycerol phosphate di(meth)acrylates, hydroxyethyl (meth)acrylate (e.g., HEMA) phosphates, bis((meth)acryloxyethyl) phosphate, ((meth)acryloxypropyl) phosphate, bis((meth)acryloxypropyl) phosphate, bis((meth)acryloxy)propyloxy phosphate, (meth)acryloxyhexyl phosphate, bis((meth)acryloxyhexyl) phosphate, (meth)acryloxyoctyl phosphate, bis((meth)acryloxyoctyl) phosphate, (meth)acryloxydecyl phosphate, bis((meth)acryloxydecyl) phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like, may be used as components in the hardenable resin system. Also monomers, oligomers, and polymers of unsaturated carbonic acids such as (meth)acrylic acids, aromatic (meth)acrylated acids (e.g., methacrylated trimellitic acids), and anhydrides thereof can be used. Certain embodiments of the present invention include an ethylenically unsaturated compound with acid functionality having at least one P—OH moiety.

Certain of these compounds are obtained, for example, as reaction products between isocyanatoalkyl (meth)acrylates and carboxylic acids. Additional compounds of this type having both acid-functional and ethylenically unsaturated components are described in U.S. Pat. Nos. 4,872,936 (Engelbrecht) and 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, polymerizable bisphosphonic acids as disclosed for example, in U.S. Provisional Application No. 60/437,106, filed Dec. 30, 2002; AA:ITA: IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. Nos. 4,259,075 (Yamauchi et al.), 4,499,251 (Omura et al.), 4,537,940 (Omura et al.), 4,539,382 (Omura et al.), 5,530,038 (Yamamoto et al.), 6,458,868 (Okada et al.), and European Pat. Application Publication Nos. EP 712,622 (Tokuyama Corp.) and EP 1,051,961 (Kuraray Co., Ltd.).

Compositions of the present invention can also include combinations of ethylenically unsaturated compounds with acid functionality as described, for example, in U.S. Provisional Application Ser. No. 60/600,658 (entitled "SELF-ADHESIVE COMPOSITIONS INCLUDING A PLURALITY OF ACIDIC COMPOUNDS"), filed on Aug. 11, 2004.

Typically, the compositions of the present invention include at least 1% by weight, more typically at least 3% by weight, and most typically at least 5% by weight ethylenically unsaturated compounds with acid functionality, based on the total weight of the unfilled composition. Typically, compositions of the present invention include at most 80% by weight, more typically at most 70% by weight, and most typically at most 60% by weight ethylenically unsaturated compounds with acid functionality, based on the total weight of the unfilled composition.

Ethylenically Unsaturated Compounds Without Acid Functionality

The compositions of the present invention may also include one or more polymerizable components in addition to the ethylenically unsaturated compounds with acid functionality, thereby forming hardenable compositions. The additional polymerizable components may be monomers, oligomers, or polymers.

In certain embodiments, the compositions are photopolymerizable, i.e., the compositions contain a photopolymerizable component and a photoinitiator (i.e., a photoinitiator system) that upon irradiation with actinic radiation initiates the polymerization (or hardening) of the composition. Such photopolymerizable compositions can be free radically polymerizable.

In certain embodiments, the compositions are chemically polymerizable, i.e., the compositions contain a chemically polymerizable component and a chemical initiator (i.e., initiator system) that can polymerize, cure, or otherwise harden the composition without dependence on irradiation with actinic radiation. Such chemically polymerizable compositions are sometimes referred to as "self-cure" compositions and may include glass ionomer cements, resin-modified glass ionomer cements, redox cure systems, and combinations thereof.

Typically, compositions of the present invention include at least 5% by weight, more typically at least 10% by weight, and most typically at least 15% by weight ethylenically unsaturated compounds without acid functionality, based on the total weight of the unfilled composition. Typically, compositions of the present invention include at most 95% by weight, more typically at most 90% by weight, and most typically at most 80% by weight ethylenically unsaturated compounds without acid functionality, based on the total weight of the unfilled composition.

Photopolymerizable Compositions

Suitable photopolymerizable compositions may include photopolymerizable components (e.g., compounds) that include ethylenically unsaturated compounds (which contain free radically active unsaturated groups). Examples of useful ethylenically unsaturated compounds include acrylic acid esters, methacrylic acid esters, hydroxy-functional acrylic acid esters, hydroxy-functional methacrylic acid esters, and combinations thereof.

Photopolymerizable compositions may include compounds having free radically active functional groups that may include monomers, oligomers, and polymers having one or more ethylenically unsaturated group. Suitable compounds contain at least one ethylenically unsaturated bond and are capable of undergoing addition polymerization. Such free radically polymerizable compounds include mono-, di- or poly-(meth)acrylates (i.e., acrylates and methacrylates) such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenol A di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired.

The polymerizable component may also contain hydroxyl groups and free radically active functional groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA). Suitable ethylenically unsaturated compounds are also available from a wide variety of commercial sources, such as Sigma-Aldrich, St. Louis. Mixtures of ethylenically unsaturated compounds can be used if desired.

Suitable photopolymerizable components include PEGDMA (polyethyleneglycol dimethacrylate having a molecular weight of approximately 400), bisGMA, UDMA (urethane dimethacrylate), GDMA (glycerol dimethacrylate), TEGDMA (triethyleneglycol dimethacrylate), bisEMA6 as described in U.S. Pat. No. 6,030,606 (Holmes), and NPGDMA (neopentylglycol dimethacrylate). Various combinations of the polymerizable components can be used if desired.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Preferred iodonium salts are the diaryl iodonium salts, e.g., diphenyliodonium chloride, diphenyliodonium hexafluorophosphate, diphenyliodonium tetrafluoroborate, and tolylcumyliodonium tetrakis(pentafluorophenyl)borate. Preferred photosensitizers are monoketones, diketones, and alpha diketones that absorb some light within a range of 400 nm to 520 nm (preferably, 450 nm to 500 nm). Typical compounds include camphorquinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Preferred electron donor compounds include substituted amines, e.g., ethyl dimethylaminobenzoate. Other suitable tertiary photoinitiator systems useful for photopolymerizing cationically polymerizable resins are described, for example, in U.S. Pat. Publication No. 2003/0166737 (Dede et al.).

Other suitable photoinitiators for polymerizing free radically photopolymerizable compositions include the class of phosphine oxides that typically have a functional wavelength range of 380 nm to 1200 nm. Preferred phosphine oxide free radical initiators with a functional wavelength range of 380 nm to 450 nm are acyl and bisacyl phosphine oxides such as those described in U.S. Pat. Nos. 4,298,738 (Lechtken et al.), 4,324,744 (Lechtken et al.), 4,385,109 (Lechtken et al.), 4,710,523 (Lechtken et al.), and 4,737,593 (Ellrich et al.), 6,251,963 (Kohler et al.); and EP Application No. 0 173 567 A2 (Ying).

Commercially available phosphine oxide photoinitiators capable of free-radical initiation when irradiated at wavelength ranges of greater than 380 nm to 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenyl-propan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Typically, the phosphine oxide initiator is present in the photopolymerizable composition in catalytically effective amounts, such as from 0.1 weight percent to 5.0 weight percent, based on the total weight of the composition.

Tertiary amine reducing agents may be used in combination with an acylphosphine oxide. Illustrative tertiary amines useful in the invention include ethyl 4-(N,N-dimethylamino)benzoate and N,N-dimethylaminoethyl methacrylate. When present, the amine reducing agent is present in the photopolymerizable composition in an amount from 0.1 weight percent to 5.0 weight percent, based on the total weight of the composition. Useful amounts of other initiators are well known to those of skill in the art.

Suitable photoinitiator systems are also described in U.S. Patent Application Ser. No. 60/754,952, filed Dec. 29, 2005.

Chemically Polymerizable Compositions

The chemically polymerizable compositions may include redox cure systems that include a polymerizable component (e.g., an ethylenically unsaturated polymerizable component) and redox agents that include an oxidizing agent and a reducing agent. Suitable polymerizable components, redox agents, optional acid-functional components, and optional fillers that are useful in the present invention are described in U.S. Pat. Publication Nos. 2003/0166740 (Mitra et al.) and 2003/0195273 (Mitra et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system (and preferably water-soluble) to permit ready dissolution in (and discourage separation from) the other components of the polymerizable composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persuluric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the polymerizable composition as described in U.S. Pat. Publication No. 2003/0195273 (Mitra et al.).

The reducing and oxidizing agents are present in amounts sufficient to permit an adequate free-radical reaction rate. This can be evaluated by combining all of the ingredients of the polymerizable composition except for the optional filler, and observing whether or not a hardened mass is obtained.

Typically, the reducing agent is present in an amount of at least 0.01% by weight, and more typically at least 0.1% by weight, based on the total weight (including water) of the components of the polymerizable composition. Typically, the reducing agent is present in an amount of no greater than 10% by weight, and more typically no greater than 5% by weight, based on the total weight (including water) of the components of the polymerizable composition.

Typically, the oxidizing agent is present in an amount of at least 0.01% by weight, and more preferably at least 0.10% by weight, based on the total weight (including water) of the components of the polymerizable composition. Typically, the oxidizing agent is present in an amount of no greater than 10% by weight, and more typically no greater than 5% by weight, based on the total weight (including water) of the components of the polymerizable composition.

The reducing or oxidizing agents can be microencapsulated as described in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an FAS glass and water and maintained in a storage-stable state.

A redox cure system can be combined with other cure systems, e.g., with a photopolymerizable composition such as described U.S. Pat. No. 5,154,762 (Mitra et al.).

Surface-Treated Basic Filler

The compositions of the invention contain a basic filler that typically comprises a metal oxide particle that has been treated so as to attach an acidic component to the particle surface. Suitable metal oxide particles for the basic filler include, but are not limited to zirconia, alumina, zinc, ytterbia, titania and the like. In some embodiments, the basic filler may be a nanofiller, i.e. comprise nano-sized particles.

The acidic component typically comprises a strong acid component, e.g. a strong carboxylic acid, a (meth)acryloyl-substituted strong carboxylic acid, a sulfonic acid, a (meth)acryloyl-substituted sulfonic acid, and combinations thereof. A strong carboxylic acid typically has a pKa equal to or less than about 5, generally in the range of 3-5. Preferably, the acidic component is a sulfonic acid (meth)acrylate derivative, such as a sulfoalkyl (meth)acrylate (e.g., sulfopropyl methacrylate).

One method for surface treating the basic filler (e.g. nanozirconia) and subsequently dispersing it into, for example, a hydrophobic resin, involves ion-exchanging a salt of a strong acid. Specifically, the filler may be prepared by mixing a metal oxide particle (e.g. zirconia) with a salt that comprises an acidic component (e.g. potassium salt of sulfopropyl methacrylate). The mixture is then exposed to an ion-exchange resin, which results in the attachment of the acidic component to the surface of the metal oxide (e.g. zirconia) particle. The resulting surface-treated filler can be used as a stabilizing agent to increase the shelf life of dental compositions, especially dental adhesive resin systems containing phosphorylated monomers. For example, when nanozirconia that has been surface treated with sulfopropyl methacrylate is added to such compositions, it can result in an increase of shelf life up to five times that of an equivalent unfilled composition.

For embodiment in which the acidic component comprises a strong carboxylic acid the carboxylic acid can be coated onto a basic filler, e.g. by standard methods, e.g. by simply mixing the acid component and the filler together in a solvent, and then incorporating the surface-coated filler into a dental resin by way of solvent exchange or by isolating the dry surface-coated filler and then incorporating the dry filler into the resin.

Additional Fillers

The compositions of the present invention can also optionally contain one or more additional fillers. Fillers may be selected from one or more of a wide variety of materials suitable for incorporation in compositions used for dental applications, such as fillers currently used in dental restorative compositions, and the like.

The filler(s) used in the compositions of the invention is preferably finely divided. The filler(s) can have a unimodal or polymodal (e.g., bimodal) particle size distribution. Typically, the maximum particle size (the largest dimension of a particle, generally, the diameter) of the filler(s) is less than 20 micrometers, more typically less than 10 micrometers, and most preferably less than 5 micrometers. Typically, the average particle size of the filler(s) is less than 0.1 micrometers, and more typically less than 0.075 micrometer.

The compositions may include a filer comprising an inorganic material. It can also be a crosslinked organic material that is insoluble in the resin system, and is optionally filled with inorganic filler. The filler(s) should in any event be nontoxic and suitable for use in the mouth. The filler(s) can be radiopaque or radiolucent. The filler typically is substantially insoluble in water.

Examples of suitable inorganic fillers are naturally occurring or synthetic materials including, but not limited to: quartz; nitrides (e.g., silicon nitride); glasses derived from, for example, Zr, Sr, Ce, Sb, Sn, Ba, Zn, and Al; feldspar; borosilicate glass; kaolin; talc; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150" and "200" silicas from Degussa Corp., Akron, Ohio and CAB-O-SIL M5 silica from Cabot Corp., Tuscola, Ill.). Examples of suitable organic filler particles include filled or unfilled pulverized polycarbonates, polyepoxides, and the like.

Suitable non-acid-reactive filler particles include quartz, submicron silica, and non-vitreous microparticles of the type described in U.S. Pat. No. 4,503,169 (Randklev). Mixtures of these non-acid-reactive fillers are also contemplated, as well as combination fillers made from organic and inorganic materials. Silane-treated zirconia-silica (Zr—Si) filler is especially useful in certain embodiments.

The composition may include acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. FAS glasses are particularly preferred. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than about 12 micrometers, typically no greater than 10 micrometers, and more typically no greater than 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

The surface of the filler particles can also be treated with a coupling agent in order to enhance the bond between the filler and the resin. The use of suitable coupling agents include gamma-methacryloxypropyltrimethoxysilane, gamma-mercaptopropyltriethoxysilane, gamma-aminopropyltrimethoxysilane, and the like.

Other suitable fillers are disclosed in U.S. Pat. Nos. 6,387,981 (Zhang et al.); 6,572,693 (Wu et al.); 6,730,156 (Windisch); and 6,899,948 (Zhang); as well as in International Publication No. WO 03/063804 (Wu et al.). Filler components described in these references include nanosized silica particles, nanosized metal oxide particles, and combinations thereof. Nanofillers are also described in U.S. Patent Publication Nos. 2005/0252413 (Kangas et al.); 2005/0252414 (Craig et al.); and 2005/0256223 (Kolb et al.).

For some embodiments of the present invention that include filler (e.g., dental adhesive compositions), the compositions typically include at least 1% by weight, more typically at least 2% by weight, and most typically at least 5% by weight filler, based on the total weight of the composition. For such embodiments, compositions of the present invention typically include at most 40% by weight, more typically at most 20% by weight, and most typically at most 15% by weight filler, based on the total weight of the composition.

For other embodiments (e.g., wherein the composition is a dental restorative or an orthodontic adhesive), compositions of the present invention typically include at least 40% by weight, more typically at least 45% by weight, and most typically at least 50% by weight filler, based on the total weight of the composition. For such embodiments, compositions of the present invention typically include at most 90% by weight, more typically at most 80% by weight, even more typically at most 70% by weight filler, and most typically at most 50% by weight filler, based on the total weight of the composition.

Other Additives

Optionally, compositions of the present invention may contain solvents (e.g., alcohols (e.g., propanol, ethanol), ketones (e.g., acetone, methyl ethyl ketone), esters (e.g., ethyl acetate), and/or other nonaqueous solvents (e.g., dimethylformamide, dimethylacetamide, dimethylsulfoxide, 1-methyl-2-pyrrolidinone)). In some embodiments, the composition may contain a water scavenger, as is described in U.S. Patent Application Ser. No. 60/754,953, filed on Dec. 29, 2005.

If desired, the compositions of the invention can contain additives such as indicators, dyes (including photobleachable dyes), pigments, inhibitors, accelerators, viscosity modifiers, wetting agents, tartaric acid, chelating agents, buffering agents, stabilizers, diluents, and other similar ingredients that will be apparent to those skilled in the art. Surfactants, for example, nonionic surfactants, cationic surfactants, anionic surfactants, and combinations thereof, may optionally be used in the compositions. Useful surfactants include non-polymerizable and polymerizable surfactants. Additionally, medicaments or other therapeutic substances can be optionally added to the dental compositions. Examples include, but are not limited to, fluoride sources, whitening agents, anticaries agents (e.g., xylitol), remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions. Combination of any of the above additives may also be employed. The selection and amount of any one such additive can be selected by one of skill in the art to accomplish the desired result without undue experimentation.

Preparation and Use of the Compositions

The dental compositions of the present invention can be prepared by combining all the various components using conventional mixing techniques. The compositions can be supplied in a variety of forms including one-part systems and multi-part systems, e.g., two-part powder/liquid, paste/liquid, paste/powder and paste/paste systems. Other forms employing multi-part combinations (i.e., combinations of two or more parts), each of which is in the form of a powder, liquid, gel, or paste are also possible. The various components of the composition may be divided up into separate parts in whatever manner is desired; however, in a redox multi-part system, one part typically contains the oxidizing agent and another part typically contains the reducing agent, though it is possible to combine the reducing agent and oxidizing agent in the same part of the system if the components are kept separated, for example, through use of microencapsulation.

The components of the composition can be included in a kit, where the contents of the composition are packaged to allow for storage of the components until they are needed.

The components of the composition can be mixed and clinically applied using conventional techniques. A curing light is generally required for the initiation of photopolymerizable compositions.

Water scavengers can be used to increase stability and/or shelf life of a wide variety of dental compositions, especially compositions (etchants, primers, bonding agents, and combinations thereof) that are used to promote the adhesion of dental materials to dental structures (e.g. hard tissues such as dentin, enamel, and bone). Exemplary dental materials include dental restoratives (e.g., composites, fillings, sealants, inlays, onlays, crowns, and bridges), orthodontic appliances, and orthodontic adhesives. The methods of the invention are particularly effective at increasing the stability and/or shelf life of non-aqueous compositions used to etch, preferably etch and prime, at least one type of dental structure (e.g., dentin, enamel, or bone). These compositions can be used with an overlying adhesive (e.g., a dental adhesive), but they more preferably can be used as the adhesive (i.e., a self-etching adhesive). In some implementations, the compositions can be in the form of a self-adhesive dental restorative or orthodontic adhesive.

Self-etching adhesives according to the invention may be applied to a dental structure using any suitable method, including any of the following:

A first method is for the practitioner to leave the structure surface wet with water after rinsing, and therefore, eliminate or partially eliminate a typical drying step before structure treatment. A non-aqueous, self-etching dental composition (e.g., a self-etching adhesive, a self-adhesive composition, or an orthodontic adhesive) can than be applied to the structure surface and cured using conventional methods.

A second method ("wet-brush" technique) is to sequentially dip a dental applicator into an aqueous diluent (e.g. water or water plus one or more additives), and then mix the wet brush with a non-aqueous, self-etching dental composition (e.g., a self-etching adhesive). The resulting aqueous mixture can than be applied to the structure surface and cured using conventional methods.

A third method is to sequentially treat a dry dental structure surface with an aqueous diluent (e.g. water or water plus one or more additives), followed by the application of a non-aqueous, self-etching dental composition (e.g., a self-etching adhesive, a self-adhesive composition, or an orthodontic adhesive). The resulting treated surface can then be further treated and cured using conventional methods.

In some embodiments of the present invention, conditions effective to cause a composition (preferably, adhesive) to etch a dental structure surface include swishing the adhesive and/or adhesive/diluent mixture with a brush to mix/rubbing dental structure surface for a time effective to etch (i.e., for at least 3 seconds), typically for at least 5 seconds, often times for at least 10 seconds, and sometimes for at least 20 seconds.

Methods of bonding a dental material to a dental structure surface preferably result in a bond to enamel or dentin (or preferably both), of at least 7 MPa, more preferably at least 15, MPa, and most preferably at least 20 MPa.

Features and advantages of this invention are further illustrated by the following examples, which are in no way intended to be limiting thereof. The particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

EXAMPLES

Test Methods

Notched Edge Shear Adhesive Test Method (Uncut Enamel)

Adhesive shear bond strength to uncut enamel for a given test sample was evaluated by the following procedure.

Preparation of Test Teeth. Bovine incisal teeth were obtained from a local slaughterhouse, the roots cut off, and the pulp removed. The teeth, free of soft tissue, were embedded in circular acrylic disks so that the labial surfaces of the teeth were exposed. The embedded teeth were stored in deionized water in a refrigerator prior to use.

Preparation of Adhesion Test Samples. The exposed labial surfaces of the embedded teeth were prophied using a prophy paste in order to clean the tooth surfaces prior to bonding.

An adhesive test sample was applied with a dental applicator brush over the exposed labial tooth surface and light cured for 10 seconds with an XL 3000 dental curing light (3M Company, St. Paul, Minn.). A 2-mm thick Teflon mold with a hole approximately 2.38 mm in diameter was clamped to the embedded tooth such that the hole in the mold exposed the flattest available area of the adhesively prepared tooth surface. A composite material, FILTEK Z250 Universal Restorative (3M Company), was filled into the hole such that the hole was completely filled, but not overfilled, and light cured per manufacturer's directions to form a "button" that was adhesively attached to the tooth.

The finished test samples were stored in deionized water at 37° C. for approximately 24 hours prior to testing.

Sample Testing. The molds were carefully removed from the embedded teeth, leaving the buttons attached to the tooth surfaces. One at a time the test samples were mounted in a holder clamped in the jaws of an Instron™ (Instron 4505, Instron Corp. Canton, Mass.) with the tooth surface oriented parallel to the direction of the pushing shear force. A metal fixture with a semicircular notched edge was attached to the Instron, and the notched edge was carefully fitted onto the button, flush with the tooth surface. The pushing shear force was started at a crosshead speed of 1 mm/min. The force in kilograms (kg) at which the bond failed was recorded, and this number was converted to a force per unit area (units of kg/cm$^2$ or MPa) using the known surface area of the button. Each reported value of adhesion to enamel or adhesion to dentin represents the average of 2 to 10 replicates.

Wire-Loop Shear Adhesive Test Method (Cut Enamel or Dentin)

Adhesive shear bond strength to cut enamel or dentin for a given test sample was evaluated by the following procedure.

Preparation of Test Teeth. Bovine incisal teeth were obtained from a local slaughterhouse, the roots cut off, and the pulp removed. The teeth, free of soft tissue, were embedded in circular acrylic disks. The embedded teeth were stored in deionized water in a refrigerator prior to use.

Preparation of Adhesion Test Samples. The embedded teeth were ground to expose a flat enamel or dentin surface using 120-grit sandpaper mounted on a lapidary wheel. Further grinding and polishing of the tooth surface was done using 320-grit sandpaper on the lapidary wheel. The teeth were continuously rinsed with water during the grinding process.

An adhesive test sample was applied with a dental applicator brush over the flat enamel or dentin surface of the prepared surface and light cured for 10 seconds with an XL 3000 dental curing light (3M Company). A 2.5-mm thick Teflon mold with a hole approximately 4.7 mm in diameter was clamped to the embedded tooth such that the hole in the mold exposed part of the adhesively prepared tooth surface. A composite material, FILTEK Z250 Universal Restorative (3M Company), was filled into the hole such that the hole was completely filled, but not overfilled, and light cured per manufacturer's directions to form a "button" that was adhesively attached to the tooth.

The finished test samples were stored in deionized water at 37° C. for approximately 24 hours prior to testing. The holes in the Teflon molds were lined with thin gelatin capsules that dissolved when stored in water, thus making it easier to remove the molds from the buttons.

Sample Testing. The molds were carefully removed from the embedded teeth, leaving the buttons attached to the tooth surfaces. One at a time the test samples were mounted in a holder clamped in the jaws of an Instron™ (Instron 4505, Instron Corp. Canton, Mass.) with the tooth surface oriented parallel to the direction of the pulling shear force. A loop of orthodontic wire (0.75-mm diameter) was placed around the button flush to the polished tooth surface, and the pulling shear force was started at a crosshead speed of 2 mm/min. The force in kilograms (kg) at which the bond failed was recorded, and this number was converted to a force per unit area (units of kg/cm$^2$ or MPa) using the known surface area of the button. Each reported value of adhesion to enamel or adhesion to dentin represents the average of 2 to 10 replicates.

| Abbreviations, Descriptions, and Sources of Materials | |
|---|---|
| Abbreviation | Description and Source of Material |
| BisGMA | 2,2-Bis[4-(2-hydroxy-3-methacryloyloxy-propoxy)phenyl]propane; CAS No. 1565-94-2 |
| TEGDMA | Triethyleneglycol dimethacrylate (Sartomer, Exton, PA) |
| UDMA | Diurethane dimethacrylate (CAS No. 41137-60-4), commercially available as Rohamere 6661-0 (Rohm Tech, Inc., Malden, MA) |
| CDMA | Citric acid dimethacrylate (See Preparation Method described herein) |
| MHP | Methacryloyloxyhexyl phosphate ($P_2O_5$ derived) (See Preparation Method described herein) |
| PM-2 | KAYAMER PM-2; Bis(methacryloxyethyl) phosphate (Nippon Kiyaku, Japan) |
| EDMAB | Ethyl 4-(N,N-dimethylamino)benzoate (Sigma-Aldrich, St. Louis MO) |
| DPIHFP | Diphenyliodonium hexafluorophosphate (Johnson Matthey, Alpha Aesar Division, Ward Hill, NJ) |
| CPQ | Camphorquinone (Sigma-Aldrich) |
| Zirconia Sol | Zirconia sol having 44.53% solids, 40.41% zirconia; prepared as described for Preparation Example 3 in U.S. patent application No. 11/078,468, filed Mar. 14, 2005 and entitled "Light Management Films with Zirconia Particles" |
| AMBERLITE IR-120(Plus) | Ion-exchange resin; strongly acidic gel-type resin useful in catalytic applications (Sigma-Aldrich) |
| SPMA K-Salt | 3-Sulfopropyl methacrylate, potassium salt (Sigma-Aldrich) |

Starting Materials Preparations

6-Methacryloxyhexyl Phosphate (MHP from $P_2O_5$)

6-Hydroxyhexyl Methacrylate Synthesis: 1,6-Hexanediol (1000.00 g, 8.46 mol, Sigma-Aldrich) was placed in a 1-liter 3-neck flask equipped with a mechanical stirrer and a narrow tube blowing dry air into the flask. The solid diol was heated to 90° C., at which temperature all the solid melted. With continuous stirring, p-toluenesulfonic acid crystals (18.95 g, 0.11 mol) followed by BHT (2.42 g, 0.011 mol) and methacrylic acid (728.49.02 g, 8.46 mol). Heating at 90° C. with stirring was continued for 5 hours during which time vacuum was applied using tap water aspirator for 5-10 minutes after each half-hour reaction time. The heat was turned off and the reaction mixture was cooled to room temperature. The viscous liquid obtained was washed with 10% aqueous sodium carbonate twice (2×240 ml), followed by washing with water (2×240 ml), and finally with 100 ml of saturated NaCl aqueous solution. The obtained oil was dried using anhydrous $Na_2SO_4$ then isolated by vacuum filtration to give 1067 g (67.70%) of 6-hydroxyhexyl methacrylate, a yellow oil. This desired product was formed along with 15-18% of 1,6-bis (methacryloyloxyhexane). Chemical characterization was by NMR analysis.

6-Methacryloxyhexyl Phosphate Synthesis: A slurry formed by mixing $P_4O_{10}$ (178.66 g, 0.63 mol) and methylene chloride (500 ml) in a 1-liter flask equipped with a mechanical stirrer under $N_2$ atmosphere. The flask was cooled in an ice bath (0-5° C.) for 15 minutes. With continuous stirring, 6-hydroxyhexyl methacrylate (962.82 g, which contained 3.78 mol of the mono-methacrylate, along with its dimethacrylate by-product as described above) was added to the flask slowly over 2 hours. After complete addition, the mixture was stirred in the ice bath for 1 hour then at room temperature for 2 hours. BHT (500 mg) was added, and then the temperature was raised to reflux (40-41° C.) for 45 minutes. The heat was turned off and the mixture was allowed to cool to room temperature. The solvent was removed under vacuum to afford 1085 g (95.5%) of 6-methacryloxyhexyl phosphate as a yellow oil. Chemical characterization was by NMR analysis.

Preparation of CDMA

In a reaction vessel fitted with a mechanical stirrer, condenser, addition funnel, and air inlet tube, 400 g of citric acid was dissolved in 2 liters of dry THF. To the resultant homogeneous solution was added 0.52 g BHT, 0.5 g TPS, and 0.98 g DBTDL. Dry air was added to the reaction mixture through the inlet tube. Then, 161.5 g (1.04 moles) of IEM was added dropwise through the addition funnel so as to maintain a reaction temperature of about 40° C. The reaction was followed by infrared spectroscopy. After all of the IEM had been added and the IR spectrum showed little to no isocyanate group, the THF was removed under vacuum from the reaction mixture. The resultant viscous liquid was dried. Nuclear magnetic resonance spectroscopy showed the presence of added methacrylate groups and the retention of carboxyl groups.

Example 1

Filler A

Zirconia Filler Surface-Treated with
3-Methacryloyloxypropyl Sulfonic Acid

Zirconia Sol (271.012 g) was mixed with isopropyl alcohol (IPA, 270.333 g) for 5 minutes. During this mixing time, AMBERLITE IR-120(Plus) ion-exchange resin was rinsed thoroughly with ethanol and decanted to clean the ion exchange resin. SPMA K-Salt (35.595) was then added to the mixture of zirconia sol and IPA and stirred 5 minutes until dissolved. To the resulting mixture was added the ethanol-rinsed ion-exchange resin in order to convert the SPMA K-Salt to the free acid and to adhere the acid-functional methacrylate (3-methacryloyloxypropyl sulfonic acid) to the surface of the zirconia nanoparticles. The resulting mixture was stirred for 20 minutes at room temperature and was then poured into glass Pyrex trays and allowed to dry for 15 minutes at 90° C. The resulting solid was then broken up with a mortar and pestle to yield a loose, free-flowing powder. The acid-treated zirconia powder was designated Example 1 (Filler A) and was found to be easily dispersible (typically with stirring and heating) in common dental resins, e.g., TEGDMA, TEGDMA/BisGMA, etc. It was found that the dispersion could be enhanced with the addition of acid-functional (meth)acrylates to the resin mixture after the initial dispersion of the filler into the resin.

Example 2

Premix of Filler A and TEGDMA

TEGDMA (22.209 g) and Filler A (10.003 g) were mixed on a hot plate at about 90° C. until the Filler A was fully dispersed. The resulting Premix was in a TEGDMA/Filler A weight ratio of about 2.22 to 1.

Example 3 and Comparative Examples 1 and 2

Adhesive Compositions With and Without Filler A

Three different self-etching adhesive compositions were prepared by mixing the ingredients shown in Table 1. The resulting compositions were designated Example 3 (containing Filler A), Comparative Example 1 (basically identical to Example 3, except with additional TEGDMA replacing the approximately 29 wt.-% of the Filler A component), and Comparative Example 2 (basically identical to CE-1, except that CDMA was substituted for a portion of the TEGDMA component).

TABLE 1

Self-Etching Adhesive Compositions

| Component (weight-percent) | Example 3 | CE-1 | CE-2 |
|---|---|---|---|
| TEGDMA/Filler A (Ex. 2) | 64.3 (29% Filler A) | — | — |
| TEGDMA | — | 61.5 | 41.5 |
| TEGDMA/CDMA (50:50 wt.-%) | — | — | 20.0 |
| UDMA | 7.49 | 10.4 | 10.4 |
| MHP | 8.76 | 8.67 | 8.67 |
| PM-2 | 17.3 | 17.3 | 17.3 |
| CPQ | 0.90 | 0.90 | 0.90 |
| EDMAB | 0.70 | 0.70 | 0.70 |
| DPIHFP | 0.50 | 0.50 | 0.50 |
| TOTAL: | 100 | 100 | 100 |

Evaluations

Shear Bond Strength Evaluations

Shear bond strength of adhesive test samples were carried out according to the Notched Edge Shear Adhesive Test Method (Uncut Enamel) and Wire-Loop Shear Adhesive Test Method (Cut Enamel or Dentin) described herein.

After initial measurements (T=0), identical test samples (in sealed glass vials with excess head space; 70+% of volume of the container) were placed into a 45° C. oven and allowed to age. At various time intervals up to 8 weeks, test samples were removed from the oven and bond strengths again measured according to the same Test Methods. Results are shown in Table 2.

The data from Table 2 show that for a cut-enamel surface, bond strength performance was extended for a significantly longer period of time in the case of Example 3 (that included acid-treated zirconia) than for the Comparative Examples 1 and 2 (that did not include acid-treated zirconia). Example 3 also showed superior Initial Bond Strength results on a dentin surface.

TABLE 2

Shear Bond Strengths (MPa) - Ageing Study at 45° C.

| Example | Substrate | Initial (T = 0) | 1 Week | 3 Weeks | 5 Weeks | 8 Weeks |
|---|---|---|---|---|---|---|
| 3 | Uncut Enamel | 18.2* | NT** | 18.0 | 17.8 | 7.7 |
| 3 | Cut Enamel | 29.2 | 28.5 | 27.8 | 30.7 | 24.5 |
| CE-1 | Cut Enamel | 30.1 | 22.0 | 20.2 | NT | 9.9 |
| CE-2 | Cut Enamel | 28.1 | 12.5 | 13.0 | NT | 10.3 |
| 3 | Dentin | 27.4 | 27.6 | 23.6 | 21.6 | 15.6 |
| CE-1 | Dentin | 16.1 | 20.8 | 19.8 | NT | 12.5 |
| CE-2 | Dentin | 20.5 | 21.2 | 17 | NT | 14.3 |

*Different lot of adhesive with identical formulation for Initial (T = 0) data point.
**NT = Not Tested Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method of making a surface-treated filler, the method comprising the steps of:
   (a) providing a metal oxide particle having a basic surface;
   (b) admixing the metal oxide particle with a salt that comprises an acidic component, thereby forming a mixture; and
   (c) contacting the mixture with an ion-exchange resin to attach the acidic component to the surface of the metal oxide particle.

2. The method of claim 1, wherein the metal oxide is selected from the group consisting of zirconia, alumina, ytterbia, titania, and zinc.

3. The method of claim 2, wherein the metal oxide is zirconia.

4. The method of claim 1, wherein the metal oxide particle comprises a nanoparticle.

5. The method of claim 1, wherein the acidic component is selected from the group consisting of carboxylic acid functionality, phosphoric acid functionality, phosphonic acid functionality, sulfonic acid functionality, and combinations thereof.

6. The method of claim 1, wherein the acidic component comprises a sulfonic acid derivative.

7. The method of claim 6, wherein the sulfonic acid derivative comprises a sulfonic acid (meth)acyrloyl derivative.

8. The method of claim 7, wherein the sulfonic acid methacryloyl derivative comprises a sulfoalkyl (meth)acrylate.

9. The method of claim 8, wherein the sulfoalkyl (meth)acrylate comprises sulfopropyl methacrylate.

* * * * *

UNITED STATES PATENT AND TRADEMARK OFFICE
CERTIFICATE OF CORRECTION

| | | |
|---|---|---|
| PATENT NO. | : 8,071,662 B2 | Page 1 of 1 |
| APPLICATION NO. | : 12/159237 | |
| DATED | : December 6, 2011 | |
| INVENTOR(S) | : Bradley D Craig | |

It is certified that error appears in the above-identified patent and that said Letters Patent is hereby corrected as shown below:

Column 2
Line 20, delete "nanozironia" and insert -- nanozirconia --, therefor.

Column 3
Line 53, delete "(methacyloyloxy)ethyl" and insert -- (methacryloyloxy)ethyl --, therefor.
Line 56, delete "methacryoyl" and insert -- methacryloyl --, therefor.

Column 7
Line 63, delete "hexacrylate," and insert -- hexaacrylate, --, therefor.

Column 9
Line 26, delete "BASE" and insert -- BASF --, therefor.

Column 10
Line 14, delete "persuluric" and insert -- persulfuric --, therefor.

Column 12
Line 48, delete "VITREBBOND," and insert -- VITREBOND, --, therefor.

Column 14
Line 39, delete "than" and insert -- then --, therefor.
Line 46, delete "than" and insert -- then --, therefor.

Column 20
Line 30, in Claim 7, delete "acyrloyl" and insert -- acryloyl --, therefor.

Signed and Sealed this
Seventh Day of February, 2012

David J. Kappos
*Director of the United States Patent and Trademark Office*